United States Patent [19]

Hung et al.

[11] Patent Number: 5,694,207
[45] Date of Patent: Dec. 2, 1997

[54] ETCH RATE MONITORING BY OPTICAL EMISSION SPECTROSCOPY

[75] Inventors: Shu Chi Hung; Hun-Jan Tao, both of Hsin-chu, Taiwan

[73] Assignee: Taiwan Semiconductor Manufacturing Company, Ltd., Hsin-chu, Taiwan

[21] Appl. No.: 762,076

[22] Filed: Dec. 9, 1996

[51] Int. Cl.⁶ .................... G01N 21/62; H01L 21/3065
[52] U.S. Cl. ................... 356/72; 356/311; 356/316
[58] Field of Search ......................... 356/311, 316, 356/72

[56] References Cited

U.S. PATENT DOCUMENTS

| | | | |
|---|---|---|---|
| 5,337,144 | 8/1994 | Strul et al. | 356/357 |
| 5,362,356 | 11/1994 | Schoenborn | 216/60 |
| 5,465,154 | 11/1995 | Levy | 356/382 |

OTHER PUBLICATIONS

S. Wolf et al. "Silicon Processing for the VLSI Era–vol 1", Lattice Press, Sunset Beach, CA. p567 undated.

*Primary Examiner*—F. L. Evans
*Attorney, Agent, or Firm*—George O. Saile; Stephen B. Ackerman

[57] ABSTRACT

The etch rate in a plasma etching system has been monitored in-situ by using optical emission spectroscopy to measure the intensities of two or more peaks in the radiation spectrum and then using the ratio of two such peaks as a direct measure of etch rate. Examples of such peaks occur at 338.5 and 443.7 nm and at 440.6 and 437.6 nm for the fluoride/SOG system. Alternately, the intensities of at least four such peaks may be measured and the product of two ratios may be used. Examples of peaks used in this manner occurred at 440.5, 497.2 and 502.3 nm, also for the fluoride/SOG system. The method is believed to be general and not limited to fluoride/SOG.

17 Claims, 3 Drawing Sheets

*FIG. 1 - Prior Art*

ETCH RATE MONITORING BY OPTICAL EMISSION SPECTROSCOPY

BACKGROUND OF THE INVENTION

(1) Field of the Invention

The invention relates to the general field of etching in gaseous plasmas, more particularly to methods for monitoring the etch rate.

(2) Description of the Prior Art

In the course of manufacturing integrated circuits, etching of various layers on the substrate surface will take place many times. In some cases a barrier layer will be present beneath the layer that is being etched so that etching stops automatically when the layer has been removed. In other cases the layer that underlies the etched layer is also susceptible to the etchant but has a different composition from the etched layer. In such cases a method for detecting the appearance of a new material among the etch byproducts can be used as an end-point detector.

In still other cases the intent is not to etch the layer in question all the way through. A case in point is when a layer, such as a spin-on-glass (SOG), is applied to the surface for the purpose of planarizing it. Normal practice would be to etch such a layer back, leaving some desired thickness of it behind. In such cases end-point detection methods are of no value and the amount of the layer that is removed must be controlled by etching at a known etch rate for a set period of time.

Prior to the present invention the method that we had been using for such a controlled etch procedure has been to first set up the etching apparatus, in this case a plasma etcher, and to fix the various parameters that are known to control etch rate, such as power, gas composition, gas pressure, etc. A control wafer (C/W) was then etched for some period of time, removed from the etcher and the etch rate (E/R) computed. If a satisfactory etch rate had been achieved with the chosen parameters they were then used in the production system and the etch times were adjusted to the particular starting thickness.

FIG. 1 is a summary, in flow chart form, of the above described methodology. As will be understood, this approach could often be time consuming as an acceptable E/R was not always achieved with the first C/W. Additionally, there was always the concern that etch rate might slowly be drifting from one run to the next because of unknown changes that were occurring in the process, so that regular recalibrations using this approach had to be performed. Typically, a new C/W took up about 300 minutes of RF discharge time. In light of this, the advantages of being able to dynamically monitor etch rate in-situ are self evident.

Some methods for in-situ etch rate monitoring have been reported in the prior art. Strul et al. (U.S. Pat. No. 5,337,144 August 1994) describe a method wherein at least one step in the surface being etched is produced as a result of the etching process. A light beam is then reflected from both the original (protected) surface and the advancing (unprotected) surface. The two reflected beams are caused to interfere, leading to an interference pattern which grows or diminishes in intensity, as etching proceeds, depending on whether interference is constructive or destructive. By timing the rate at which the interference pattern changes its intensity the etch rate is calculated. This method is unsuitable for measuring the etch rate of unprotected planar layers such as ours. Additionally, it is not truly dynamic, representing only the average rate between the appearance of peaks and/or valleys in the interference pattern.

A different approach, which is suitable for use with planar unprotected layers, has been described by Levy (U.S. Pat. No. 5,465,154 November 1995). Levy's method is limited to transparent films and is basically a dynamic thickness measurement which, when differentiated over time, leads to an etch rate. Thickness is measured by allowing light beams reflected from the upper and lower surfaces of the layer to interfere. Given the angle of incidence, the wavelength of the light, and the refractive index of the film, the thickness may be calculated. In practice, it is necessary to observe the time between at least two maxima or minima in the interference pattern before an etch rate can be computed.

Since the present invention is based on the use of optical emission spectroscopy (OES), it should be noted that OES is widely used for end point detection during plasma etching but not, to our knowledge, for measuring etch rate. Use of OES for end point detection is described in, for example, "Silicon processing for the VLSI era—vol. 1" by S. Wolf and R. N. Tauber on page 567. The method depends on the sudden increase in the intensity of a monitored species when the layer being etched changes its composition. Following standard practice in the spectroscopy art, the absolute intensity of the monitored species is not measured but rather its ratio to the intensity of some background species (such as the etchant gas) that should not be affected by any change in the composition of the etched layer.

SUMMARY OF THE INVENTION

It has been an object of the present invention to provide a method for the in-situ monitoring of etch rate during plasma etching.

Another object has been that said method be independent of local fluctuations in plasma intensity.

A still further object has been that the method work for layers that are uniformly planar, there being no steps in the surface that is being etched, as well as for non-planar surfaces.

Yet another object of the present invention is that it not be restricted to transparent layers.

An additional object has been that the measurement should be effectively instaneous.

These objects have been achieved by using optical emission spectroscopy to measure the intensities of two or more peaks in the radiation spectrum and then using the ratio of two such peaks as a direct measure of etch rate. Examples of such peaks occur at 338.5 and 443.7 nm and at 440.6 and 437.6 nm for the fluoride/SOG system. Alternately, the intensities of at least four such peaks may be measured and the product of two ratios may be used. Examples of peaks used in this manner occurred at 440.5, 497.2 and 502.3 nm, also for the fluoride/SOG system.

DESCRIPTION OF THE PREFERRED EMBODIMENTS

Figure 1:
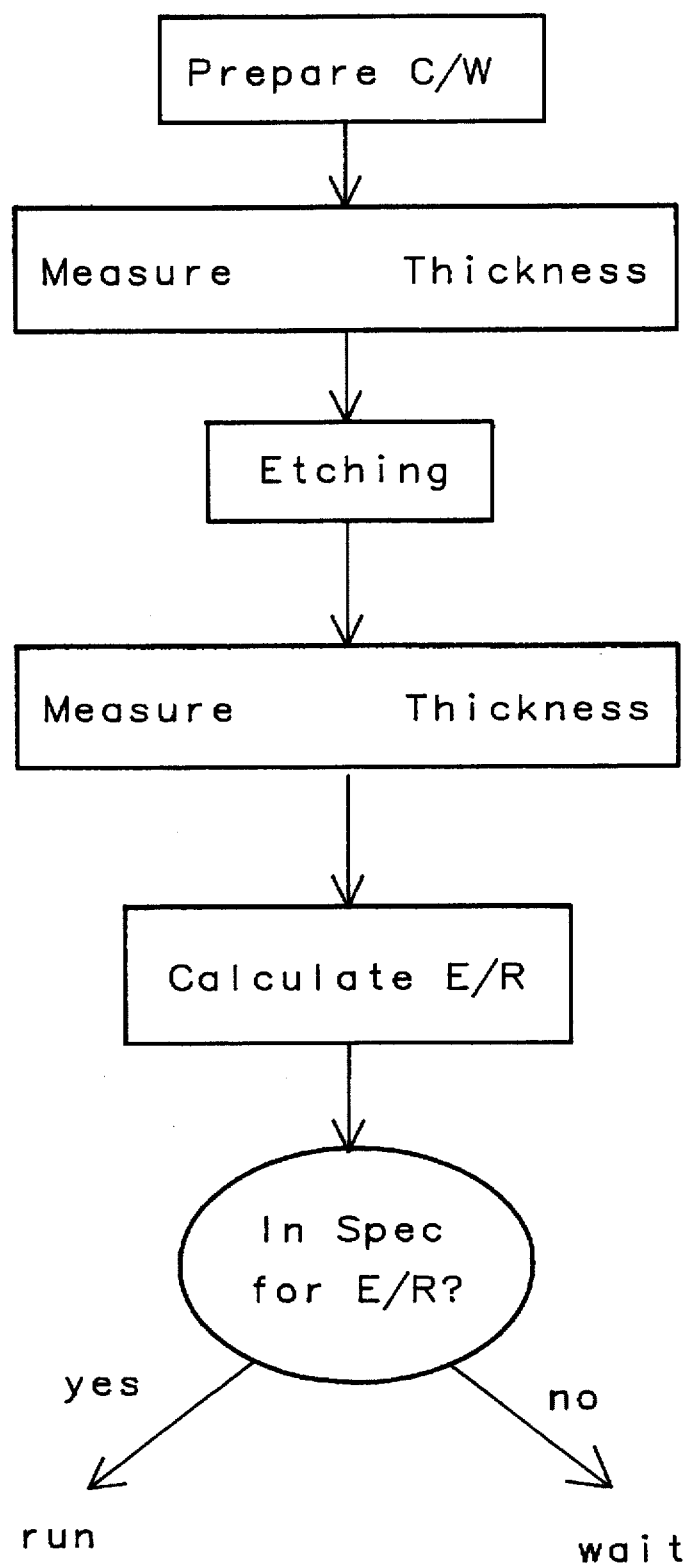
FIG. 1 is a flow chart representation of the etch monitoring method that we used prior to the present invention.
Figure 2:
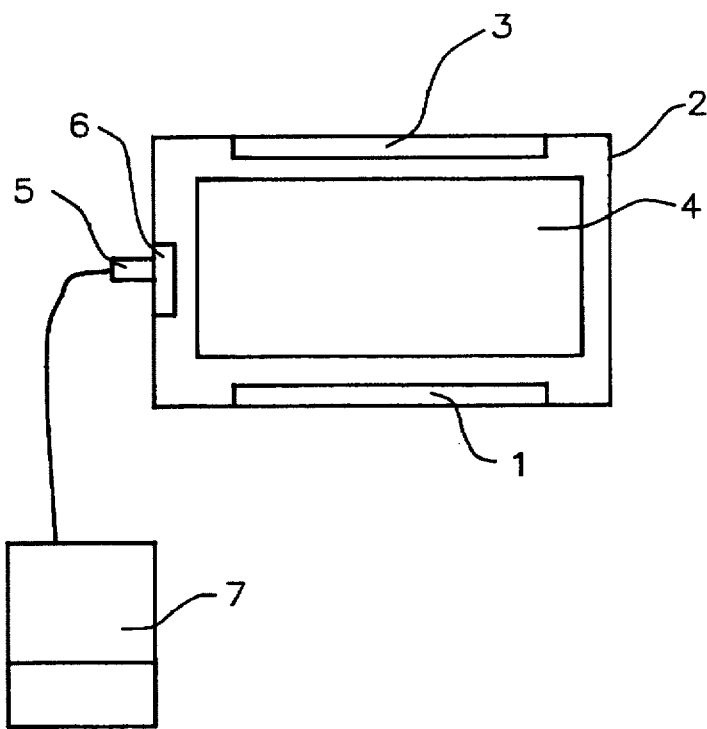
FIG. 2 is a schematic representation of the apparatus used to implement the method of the present invention.

Referring now to FIG. 2, substrate 1 (for example a silicon wafer), bearing the layer that is to be etched (typically between about 5500 and 5800 Angstroms thick), is placed inside plasma etching chamber 2. Through the application of suitable power to electrode 3 a gaseous plasma 4 is excited. 4 is composed of gases that, when in plasma form, are highly reactive with the layer to be etched. The latter could be a layer of SOG, silicon oxide, silicon nitride, aluminum oxide, etc. while the gases in the plasma could, for example, include argon, nitrogen, trifluoromethane, and carbon tetrafluoride. Light emitted by plasma 4 is seen by spectrophotometer 5 which monitors the plasma through viewing window 6 and can measure the intensity of the emitted radiation over a wide range of wavelengths. In our work we have used a SOFIZ spectrophotometer which operates over a range of from 400 to 600 nanometers.

As a result of experimentation we have found that the intensities of certain peaks in the radiation spectrum are directly proportional to the etch rate of the layer that is being consumed by the plasma. As a protection against possible unknown fluctuations of the intensity of the discharge as a whole, changes in the transparency of window 6, etc., we also measure the intensity of a peak that we observe to be unaffected by the etch rate and use the ratio of these two numbers as a direct measure of the etch rate.

At the present time the peaks that we have determined to be suitable for measuring etch rate have been found by trial and error so a discussion of the physical mechanisms involved in our method would only be speculative. However, we believe the method to be a general one, not restricted to the particular combination of etchant and etched layer that we have been using.

Figure 3A:
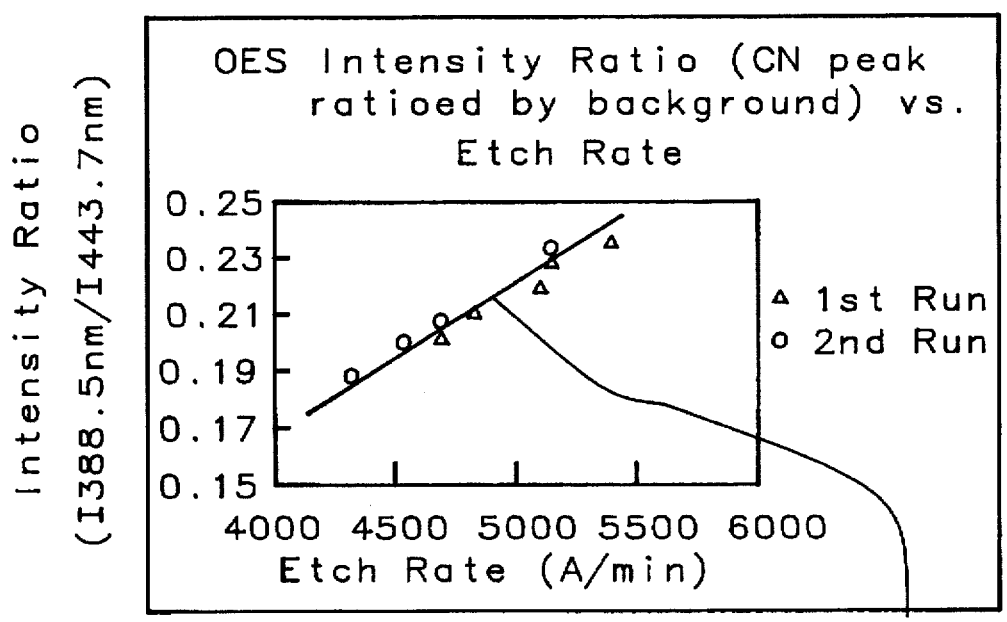
FIGS. 3a and b show curves of the intensity ratios of selected peaks as a function of independently measured etch rate.
Figure 3B:
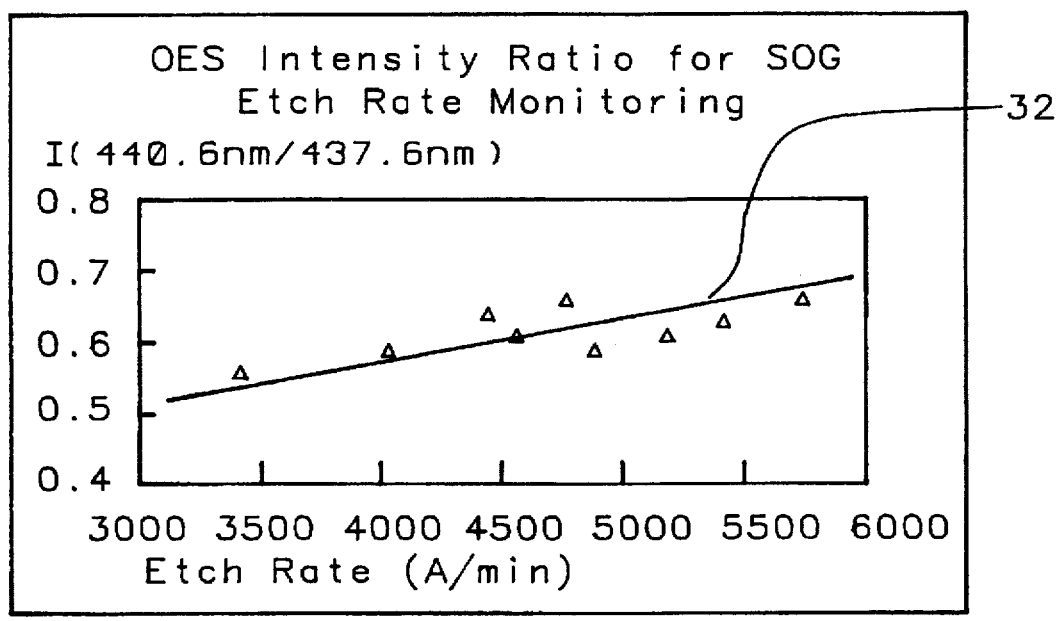

In FIGS. 3a and 3b we show some data that illustrate the efficacy of our method. Curve 31 shows a plot of etch rate (measured using a C/W as described earlier) vs. the intensity ratio for the peaks at 388.5 and 443.7 nanometers while curve 32 shows a plot of etch rate (also measured using a C/W as described earlier) vs. the intensity ratio for peaks at 440.6 and 437.6 nanometers. For both figures the material being etched was SOG while the etchant gas contained trifluoromethane, carbon tetrafluoride, and argon excited over a range of power from about 800 to about 1,000 watts, at a pressure between about 700 and 900 millitorr. As can be seen, the measured etch rates cover a range of from about 4,500 to about 5,100 Angstroms per minute.

Figure 4:
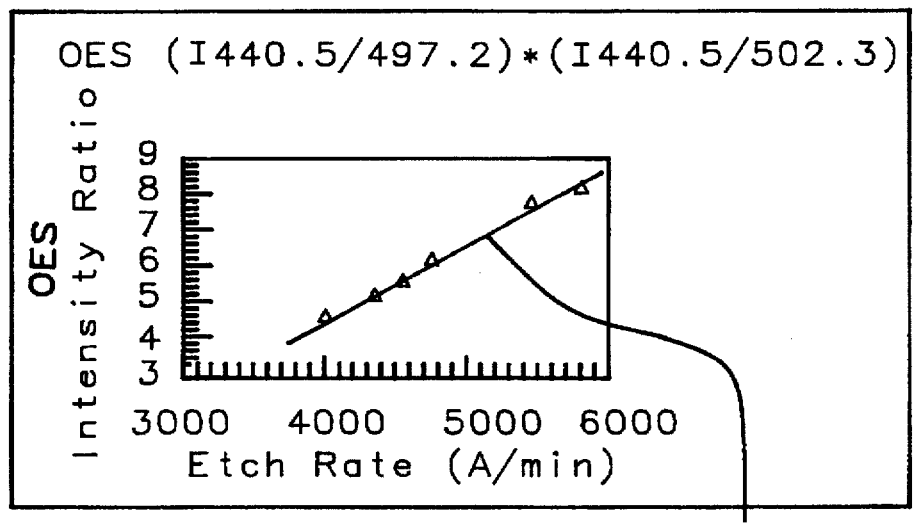
FIG. 4 shows a curve of the product of two different peak intensity ratios as a function of independently measured etch rate.

Curves 31 and 32 fit the observed data fairly well and either one could be used for the in-situ measurement of etch rate during plasma etching. We have also found that by using a slightly more complicated number, derived by multiplying together two ratios such as those used in FIGS. 3a and 3b, an even better fit against the independently measured etch rate can be obtained. This is shown in FIG. 4 which uses the product of the intensity ratios of the peaks at 440.5 and 497.2 nanometers times the intensity ratios of the peaks at 440.5 and 502.3 nanometers. As can be seen, the fit for curve 41 is extremely good so, using the product of two intensity ratios, provides an excellent method for the in-situ measurement of etch rate.

We note that all the above mentioned steps are readily automated so that spectrophotometer 5 can be programmed to continually read the intensities at the chosen peaks and then feed the data into computer 7 where the intensity ratios, products, etc. may be computed. Then, using previously determined data, such as seen in FIGS. 3a, 3b, or 4, the instantaneous etch rate can be computed. This, in turn, may be integrated over time so that the amount of removed material is always known, allowing the etching process to be terminated at exactly the right moment.

While the invention has been particularly shown and described with reference to the preferred embodiments thereof, it will be understood by those skilled in the art that various changes in form and details may be made without departing from the spirit and scope of the invention.

What is claimed is:

1. A method for in-situ monitoring the etch rate of a layer, comprising:

providing a silicon substrate bearing said layer;

providing a gaseous plasma that emits radiation and that etches said layer;

providing power to form the plasma and inserting the substrate therein, thereby causing etching to take place;

measuring intensity values for said radiation at wavelengths 388.5 and 443.7 nanometers of the radiation; and computing the quotient of the intensity at 388.5 nanometers divided by the intensity at 443.7 nanometers, thereby providing a number that is proportional to said etch rate.

2. The method of claim 1 wherein said layer is spin-on-glass or silicon oxide.

3. The method of claim 1 wherein said plasma comprises argon, nitrogen, and a gas selected from the group consisting of trifluoro methane and carbon tetrafluoride.

4. The method of claim 1 wherein the power provided to form the plasma is between about 800 and 1,000 watts.

5. The method of claim 1 wherein the etch rate is between about 4,500 and 5,100 Angstroms per minute.

6. A method for in-situ monitoring the etch rate of a layer, comprising:

providing a substrate bearing said layer;

providing a gaseous plasma that emits radiation and that etches said layer;

providing power to form the plasma and inserting the substrate therein, thereby causing etching to take place;

measuring first and second intensity values for said radiation, at first and second wavelengths of the radiation respectively;

measuring third and fourth intensity values for said radiation, at third and fourth wavelengths of the radiation respectively;

computing a first quotient comprising the first intensity value divided by the second intensity value;

computing a second quotient comprising the third intensity value divided by the fourth intensity value; and computing the product of the first quotient multiplied by the second quotient, thereby providing a number that is proportional to said etch rate.

7. The method of claim 6 wherein the first wavelength is at 440.5 nanometers, the second wavelength is at 497.2 nanometers, the third wavelength is at 440.5 nanometers, the fourth wavelength is at 502.3 nanometers.

8. The method of claim 6 wherein the substrate is a silicon wafer.

9. The method of claim 6 wherein said layer is spin-on-glass or silicon oxide.

10. The method of claim 6 wherein said plasma comprises argon, nitrogen, and a gas selected from the group consisting of trifluoro methane and carbon tetrafluoride.

11. The method of claim 6 wherein the power provided to form the plasma is between about 800 and 1,000 watts.

12. The method of claim 6 wherein the etch rate is between about 4,500 and 5,100 Angstroms per minute.

13. A method for in-situ monitoring the etch rate of a layer, comprising:

providing a silicon substrate bearing said layer;

providing a gaseous plasma that emits radiation and that etches said layer;

providing power to form the plasma and inserting the subtrate therein, thereby causing etching to take place;

measuring intensity values for said radiation at wavelengths 440.6 and 437.6 nanometers of the radiation; and computing the quotient of the intensity at 440.6 nanometers divided by the intensity at 437.6 nanometers, thereby providing a number that is proportional to said etch rate.

14. The method of claim 13 wherein said layer is spin-on-glass or silicon oxide.

15. The method of claim 13 wherein said plasma comprises argon, nitrogen, and a gas selected from the group consisting of trifluoromethane and carbon tetrafluoride.

16. The method of claim 13 wherein the power provided to form the plasma is between about 800 and 1,000 watts.

17. The method of claim 13 wherein the etch rate is between about 4,500 and 5,100 Angstroms per minute.

* * * * *